(12) United States Patent
Binggeli et al.

(10) Patent No.: US 7,098,228 B2
(45) Date of Patent: Aug. 29, 2006

(54) INDOLYL DERIVATIVES

(75) Inventors: Alfred Binggeli, Binningen (CH); Uwe Grether, Loerrach (DE); Hans Hilpert, Munchenstein (CH); Georges Hirth, Huningue (FR); Bernd Kuhn, Riehen (CH); Hans-Peter Maerki, Basel (CH); Markus Meyer, Neuenburg (DE); Peter Mohr, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 388 days.

(21) Appl. No.: 10/719,556

(22) Filed: Nov. 21, 2003

(65) Prior Publication Data

US 2004/0106657 A1   Jun. 3, 2004

(30) Foreign Application Priority Data

Nov. 25, 2002  (EP)  .................................. 02026366

(51) Int. Cl.
*A61K 31/425*  (2006.01)
*A61K 31/42*   (2006.01)
*A61K 31/40*   (2006.01)
*C07D 277/30*  (2006.01)
*C07D 263/30*  (2006.01)

(52) U.S. Cl. ...................... 514/365; 514/374; 514/419; 548/204; 548/235; 548/465

(58) Field of Classification Search ................ 514/365, 514/374, 419; 548/204, 235, 465
See application file for complete search history.

(56) References Cited

U.S. PATENT DOCUMENTS

| | | | |
|---|---|---|---|
| 4,011,326 A | 3/1977 | Jensen | |
| 4,598,089 A | 7/1986 | Hadvary et al. | |
| 5,089,514 A | 2/1992 | Hulin | |
| 5,599,826 A | 2/1997 | Mertens et al. | |
| 5,811,439 A | 9/1998 | Ogawa | |
| 5,856,529 A | 1/1999 | Catt et al. | |
| 6,004,996 A | 12/1999 | Shah et al. | |
| 6,121,397 A | 9/2000 | MacLeod et al. | |
| 6,291,685 B1 | 9/2001 | Junghans et al. | |
| 6,441,185 B1 | 8/2002 | Kühnle et al. | |
| 6,903,104 B1 * | 6/2005 | Chen et al. | 514/254.09 |
| 6,903,117 B1 * | 6/2005 | Farina et al. | 514/323 |
| 6,911,465 B1 * | 6/2005 | Faull et al. | 514/419 |
| 6,933,316 B1 * | 8/2005 | Hsieh et al. | 514/419 |
| 6,949,566 B1 * | 9/2005 | Watanabe et al. | 514/307 |
| 6,960,605 B1 * | 11/2005 | Wagle et al. | 514/365 |

FOREIGN PATENT DOCUMENTS

| | | |
|---|---|---|
| EP | 0 047 358 B1 | 3/1982 |
| EP | 185359 | 6/1986 |
| EP | 189577 | 8/1986 |
| EP | 443449 | 8/1991 |
| EP | 524495 | 1/1993 |
| EP | 0 780 389 | 6/1997 |
| EP | 0903343 | 3/1999 |
| EP | 1 078 923 | 2/2001 |
| WO | WO 91/19702 | 12/1991 |
| WO | WO 94/01420 | 1/1994 |
| WO | WO 94/13650 | 6/1994 |
| WO | WO 95/17394 | 6/1995 |
| WO | WO 97/25042 | 7/1997 |
| WO | WO 99/08501 | 2/1999 |
| WO | WO 99/10339 | 3/1999 |
| WO | WO 00 08002 | 2/2000 |
| WO | WO 00/09122 | 2/2000 |
| WO | WO 00/09123 | 2/2000 |
| WO | WO 0100603 | 1/2001 |
| WO | WO 02 16331 | 2/2002 |
| WO | WO 02 092084 | 11/2002 |
| WO | WO 03/004458 | 1/2003 |
| WO | WO 03/053976 | 7/2003 |

OTHER PUBLICATIONS

Keller and Wahli: Trends Endocrin. Metab. (1993); 4:291-296.
MacDougald and Lane: Current Biology vol. 5 pp. 618-621 (1995).
Guerre-Millo, et. al.; J Biol Chem2000; 275: 16638-16642.
Balfour, et. al.; Drugs 57 (1999) 921-930.
Haigh et. al., Tetrahedron: Asymmetry, 10, pp. 1353-1367.
Gotteland et al., Synlett, 9 pp. 931-932 (1995).
Hulin et al., J. Med. Chem., 39, pp. 3897-3907 (1996).
Nicolaou et al., J. Am. Chem. Soc., 122, pp. 3830-3838 (2000).
Nichols et al., Anal. Biochem., 257, pp. 112-119 (1998).
Einsiedel et. al., Bioorg. Med. Chem. Lett., 10, pp. 2041-2044 (2000).
Goto et al., Chem. Pharm. Bull., 19, pp. 2050-2057 (1971).

(Continued)

*Primary Examiner*—Deborah C. Lambkin
(74) *Attorney, Agent, or Firm*—George W. Johnston; Dennis P. Tramaloni; Samuel H. Megerditchian

(57) ABSTRACT

The present invention provides compounds of formula I

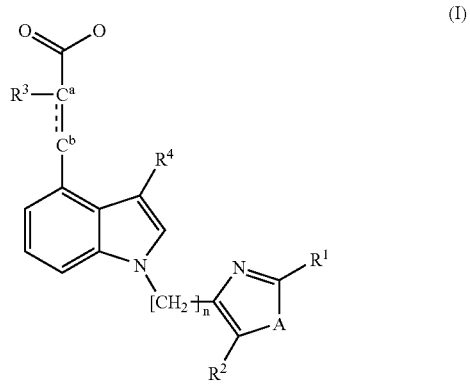

as well as pharmaceutically acceptable salts and esters thereof, wherein $R^1$ to $R^4$, A and n have the significance given in the specification. The compounds or their salts may be administered to a patient for treating non-insulin dependent diabetes mellitus.

20 Claims, No Drawings

OTHER PUBLICATIONS

Reichstein et al., Helvetica Chimica Acta, 16, pp. 121-129 (1933).
Diels et al., chem.. Ber., 48, pp. 897-905 (1915).
Wightman et al., J. Org. chem.., 43, pp. 2167-2170 (1978).
Musser et al., J. Med. Chem. 30, pp. 62-67 (1987).
Rahman et al., J. Chem. Soc. Perkin Trans. 1, 12, pp. 2973-2977 (1983).
Kelly et. al., J. Am. Chem. Soc., 110, pp. 6471-6480 (1988).
Kneen et al., Synthetic Communications, 16, pp. 1635-1640 (1986).
Kim et al., Can. J. Chem., 60, pp. 2093-2098 (1982).
Pàrkànyi et al., Monatsh. Chem., 123, pp. 637-645 (1992).
STN International ® CAPLUS Database, Accession No. 2000; 117035; Collins et al., WO 2000008002, abstract.
Malamas, MS et al, Eur. J. Med. Chem. vol. 36, No. 1 (2001) pp. 31-42.
Hulin, B. et al., Current Pharmaceutical Design, vol. 2 (1996) pp. 85-102.
Oplinger, et. al., ACS National Meeting, San Diego, Apr. 1-5, 2001, Poster 238, Division of Medicinal Chemistry, Section C.
Gustavsson, et. al., Chemical Abstracts, vol. 138, No. 106,504 (2003).
Rami H K et al: "Synthetic ligands for PPAR gamma-review of patent literature 1994-1999" Expert Opinion on Therapeutic Patents, vol. 10(5) 2000, pp. 623-633.
Henke B R et al, Bioorganic & Medicinal Chemistry Letters vol. 9,(23) pp. 3329-3334 (Dec. 1999).
Lean, M.E.J., et al, European Journal of Clinical Pharmacology, vol. 25, No. 1, pp. 41-45 (1983).

* cited by examiner

INDOLYL DERIVATIVES

BACKGROUND OF THE INVENTION

Peroxisome Proliferator Activated Receptors (PPAR's) are members of the nuclear hormone receptor super family, which are ligand-activated transcription factors regulating gene expression. Various subtypes thereof have been identified and cloned. These include PPARα, PPARβ also known as PPARδ), and PPARγ. There exist at least two major isoforms of PPARγ. While PPARγ1 is ubiquitously expressed in most tissues, the longer isoform PPARγ2 is almost exclusively found in adipocytes. In contrast, PPARα is predominantly expressed in the liver, kidney and heart. PPAR's modulate a variety of body responses including glucose- and lipid-homeostasis, cell differentiation, inflammatory responses and cardiovascular events.

Diabetes is a disease in which a patient's ability to control glucose levels in blood is impaired, because he has partially lost the ability to respond properly to the action of insulin. In type II diabetes (T2D), often referred to as non-insulin dependent diabetes mellitus (NIDDM), which afflicts 80–90% of all diabetic patients in developed countries, the Isles of Langerhans in the pancreas still produce insulin. However, the target organs, mainly muscle, liver and adipose tissue, exhibit a profound resistance to insulin stimulation, and the body compensates by producing unphysiologically high levels of insulin. In later stage of disease, however, insulin secretion decreases due to exhaustion of the pancreas. In addition to that T2D is a metabolic-cardiovascular disease sysndrome. Among the comorbidities associated with T2D are for example insulin resistance, dyslipidemia, hypertension, endothelial dysfunction and inflammatory atherosclerosis.

Current first line treatment for diabetes generally involves low fat—and glucose—diet and exercise. However, compliance can be moderate and as the disease progresses, treatment with hypoglycemic drugs, e.g. sulfonylureas or metformin, becomes necessary. A promising new class of drugs has recently been introduced that resensitizes patients to their own insulin (insulin sensitizers), thereby reverting blood glucose and triglyceride levels to normal, and thus abolishing, or at least reducing, the requirement for exogenous insulin. Pioglitazone (Actos™) and rosiglitazone (Avandia™) belong to the thiazolidinediones (TZD) class of PPARγ-agonists and were the first representatives approved for NIDDM in several countries. These compounds, however, suffer from side effects including rare but severe liver toxicity (as seen with troglitazone), and they increase body weight in humans. Therefore, new, better and more efficacious drugs for the treatment of NIDDM are urgently needed. Recent studies provide evidence that a coagonism on PPARα and PPARγ would result in compounds with enhanced therapeutic potential, i. e. with an improved lipid profile effect on top of the normalization of glucose- and insulin-levels (Keller and Wahli: Trends Endocrin. Metab. 1993; 4:291–296, Macdonald and Lane: Current Biology Vol. 5 pp. 618–621 (1995)).

SUMMARY OF THE INVENTION

The present invention provides the compounds of formula I

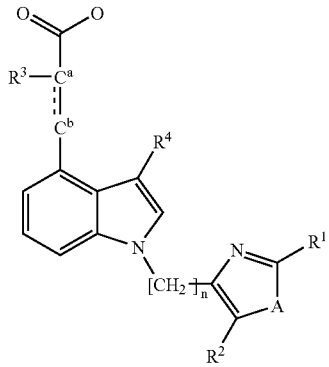

(I)

and pharmaceutically acceptable salts and esters thereof, wherein $R^1$ is unsubstituted naphthyl, unsubstituted phenyl, phenyl substituted with one or more substituents each independently selected from halogen, trifluoromethyl, amino, alkyl, alkoxy, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, hydroxy, alkyl substituted with one to three halogen atoms, and nitro, unsubstituted heteroaryl which contains one or two hetero atoms selected from nitrogen, oxygen and sulfur, or substituted heteroaryl which is heteroaryl which contains one or two hetero atoms selected from nitrogen, oxygen and sulfur and which is substituted on at least one carbon atom with a group independently selected from halogen, alkyl, alkoxy, cyano, haloalkyl and trifluoromethyl;

$R^2$ is hydrogen, alkyl or cycloalkyl;

$R^3$ is alkoxy or alkoxy substituted with one to three halogen atoms;

$R^4$ is hydrogen, alkyl or cycloalkyl;

A is oxygen or sulfur;

n is 1, 2 or 3;

wherein the bond between the carbon atoms $C^a$ and $C^b$ is a carbon carbon single or double bond.

The compounds of formula I and their pharmaceutically acceptable salts and esters are insulin sensitizers, particularly PPAR activators.

DETAILED DESCRIPTION OF THE INVENTION

The present invention provides the compounds of formula I

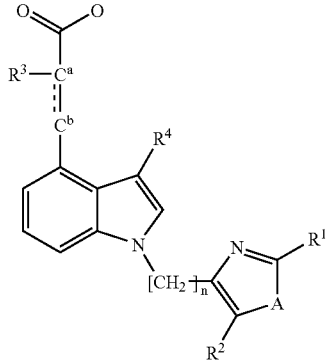

(I)

and pharmaceutically acceptable salts and esters thereof, wherein
R$^1$ is aryl or heteroaryl;
R$^2$ is hydrogen, alkyl or cycloalkyl;
R$^3$ is alkoxy or alkoxy substituted with one to three halogen atoms;
R$^4$ is hydrogen, alkyl or cycloalkyl;
A is oxygen or sulfur;
n is 1, 2 or 3;

wherein the bond between the carbon atoms C$^a$ and C$^b$ is a carbon carbon single or double bond.

The compounds of the present invention bind to and activate both, PPARα and PPARγ, simultaneously and very efficiently. Therefore, these compounds combine the anti-glycemic effect of PPARγ activation with the anti-dyslipidemic effect of PPARα activation. Consequently, plasma glucose and insulin are reduced (=insulin sensitization), triglycerides lowered and HDL cholesterol increased (=improved lipid profile). In addition, such compounds may also lower LDL cholesterol, decrease blood pressure and counteract inflammatory atherosclerosis. Since multiple facets of the T2D disease syndrome are addressed by PPARα and γ coagonists, they are expected to have an enhanced therapeutic potential compared to the compounds already known in the art.

Accordingly, the compounds of formula I can be used in the prophylaxis and/or treatment of diabetes, particularly non-insulin dependent diabetes mellitus, elevated blood pressure, increased lipid and cholesterol levels, atherosclerotic diseases or metabolic syndrome.

In the present description the term "alkyl", alone or in combination, signifies a straight-chain or branched-chain alkyl group with 1 to 8 carbon atoms, preferably a straight or branched-chain alkyl group with 1 to 6 carbon atoms and particularly preferred a straight or branched-chain alkyl group with 1 to 4 carbon atoms. Examples of straight-chain and branched C$_1$–C$_8$ alkyl groups are methyl, ethyl, propyl, isopropyl, butyl, isobutyl, tert.-butyl, the isomeric pentyls, the isomeric hexyls, the isomeric heptyls and the isomeric octyls, preferably methyl and ethyl and most preferred methyl.

The term "cycloalkyl", alone or in combination, signifies a cycloalkyl ring with 3 to 8 carbon atoms and preferably a cycloalkyl ring with 3 to 6 carbon atoms. Examples of C$_3$–C$_8$ cycloalkyl are cyclopropyl, methyl-cyclopropyl, dimethylcyclopropyl, cyclobutyl, methyl-cyclobutyl, cyclopentyl, methyl-cyclopentyl, cyclohexyl, methyl-cyclohexyl, dimethyl-cyclohexyl, cycloheptyl and cyclooctyl, preferably cyclopropyl.

The term "alkoxy", alone or in combination, signifies a group of the formula allyl-O- in which the term "alkyl" has the previously given significance, such as methoxy, ethoxy, n-propoxy, isopropoxy, n-butoxy, isobutoxy, sec. butoxy and tert.butoxy, 2-hydroxyethoxy, 2-methoxyethoxypreferably methoxy and ethoxy and most preferred methoxy.

The term "aryl", alone or in combination, signifies a phenyl or naphthyl group, preferably a phenyl group which optionally carries one or more substituents each independently selected from halogen, trifluoromethyl, amino, alkyl, alkoxy, alkylcarbonyl, cyano, carbamoyl, alkox-ycarbamoyl, methylendioxy, carboxy, alkoxycarbonyl, aminocarbonyl, alkyaminocarbonyl, dialkylaminocarbonyl, hydroxy, alkyl substituted with one to three halogen atoms, nitro and the like, such as phenyl, fluorophenyl, chlorophenyl, methoxyphenyl, isopropoxyphenyl, methylphenyl, ethylphenyl, isopropylphenyl, tert-butylphenyl, phenyl substituted with trifluoromethyl, phenyl substituted with two methyl groups, phenyl substituted with two methoxy groups, phenyl substituted with two fluoro atoms, phenyl substituted with two chloro atoms, phenyl substituted with methyl and fluoro or phenyl substituted with three methoxy groups.

The term "aralkyl", alone or in combination, signifies an alkyl or cycloalkcyl group as previously defined in which one or more, preferably one hydrogen atom has been replaced by an aryl group as previously defined. Preferred are benzyl, benzyl substituted with hydroxy, alkoxy or halogen, preferably fluorine. Particularly preferred is benzyl.

The term "amino", alone or in combination, signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two nitrogen substitutents together forming a ring, such as, for example, —NH$_2$, methylamino, ethylamino, dimethylamino, diethylamino, methyl-ethylamino, pyrrolidin-1-yl or piperidino etc., preferably amino, dimethylamino and diethylamino and particularly primary amino.

The term "halogen" alone or in combination signifies fluorine, chlorine, bromine or iodine and preferably fluorine, chlorine or bromine. Particularly preferred is fluorine or chlorine.

The term "carbonyl", alone or in combination signifies the —C(O)— group.

The term "cyano", alone or in combination signifies the group —CN.

The term "heteroaryl", alone or in combination, signifies aromatic 5- to 10-membered heterocycle which contains one or more, preferably one or two hetero atoms selected from nitrogen, oxygen and sulfur, wherein sulfur are preferred. If desired, it can be substituted on one or more carbon atoms by halogen, alkyl, alkoxy, cyano, haloalkyl and/or trifluoromethyl. Preferred heteroaryl cycles are pyridinyl or thiophen-2-yl optionaly substituted by one or more, preferably one or two substituents independently selected from halogen, alkyl, alkoxy, cyano, haloalkyl and trifluoromethyl. Particularly preferred is thiophen-2-yl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, succinic acid, ftimaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula I can also be present in the form of zwitterions. Particularly preferred pharmaceutically acceptable salts of compounds of formula I are the sodium salts.

The compounds of formula I can also be solvated, e.g. hydrated. The solvation can be effected in the course of the manufacturing process or can take place e.g. as a consequence of hygroscopic properties of an initially anhydrous compound of formula I (hydration). The term pharmaceutically acceptable salts also includes physiologically acceptable solvates.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Further preferred pharmaceutically acceptable esters are alkyl, hydroxy-alkyl, alkoxy-alkyl, amino-alkyl, mono- or di-alkyl-amino-alkyl, morpholino-alkyl, pyrrolidino-alkyl, piperidino-alkyl, piperazino-alkyl, alkyl-piperazino-alkyl and aralkyl esters.

Additionally, any physiologically acceptable equivalents of the compounds of general formula (I), similar to the metabolically labile esters, which are capable of producing the parent compounds of general formula (I) in vivo, are within the scope of this invention.

The term "lipase inhibitor" refers to compounds which are capable of inhibiting the action of lipases, for example gastric and pancreatic lipases. For example orlistat and lipstatin as described in U.S. Pat. No. 4,598,089 are potent inhibitor of lipases. Lipstatin is a natural product of microbial origin, and orlistat is the result of a hydrogenation of lipstatin. Other lipase inhibitors include a class of compound commonly referred to as panclicins. Panclicins are analogues of orlistat (Mutoh et al, 1994). The term "lipase inhibitor" refers also to polymer bound lipase inhibitors for example described in International Patent Application WO99/34786 (Geltex Pharmaceuticals Inc.). These polymers are characterized in that they have been substituted with one or more groups that inhibit lipases. The term "lipase inhibitor" also comprises pharmaceutically acceptable salts of these compounds. The term "lipase inhibitor" preferably refers to orlistat.

Orlistat is a known compound useful for the control or prevention of obesity and hyperlipidemia. See, U.S. Pat. No. 4,598,089, issued Jul. 1, 1986, which also discloses processes for making orlistat and U.S. Pat. No. 6,004,996, which discloses appropriate pharmaceutical compositions. Further suitable pharmaceutical compositions are described for example in International Patent Applications WO 00/09122 and WO 00/09123. Additional processes for the preparation of orlistat are disclosed in European Patent Applications Publication Nos. 185,359, 189,577, 443,449, and 524,495.

Orlistat is preferably orally administered from 60 to 720 mg per day in divided doses two to three times per day. Preferred is wherein from 180 to 360 mg, most preferably 360 mg per day of a lipase inhibitor is administered to a subject, preferably in divided doses two or, particularly, three times per day. The subject is preferably an obese or overweight human, i.e. a human with a body mass index of 25 or greater. Generally, it is preferred that the lipase inhibitor be administered within about one or two hours of ingestion of a meal containing fat. Generally, for administering a lipase inhibitor as defined above it is preferred that treatment be administered to a human who has a strong family history of obesity and has obtained a body mass index of 25 or greater.

Orlistat can be administered to humans in conventional oral compositions, such as, tablets, coated tablets, hard and soft gelatin capsules, emulsions or suspensions. Examples of carriers which can be used for tablets, coated tablets, dragees and hard gelatin capsules are lactose, other sugars and sugar alcohols like sorbitol, mannitol, maltodextrin, or other fillers; surfactants like sodium lauryle sulfate, Brij 96, or Tween 80; disintegrants like sodium starch glycolate, maize starch or derivatives thereof; polymers like povidone, crospovidone; talc; stearic acid or its salts and the like. Suitable carriers for soft gelatin capsules are, for example, vegetable oils, waxes, fats, semi-solid and liquid polyols and the like. Moreover, the pharmaceutical preparations can contain preserving agents, solubilizers, stabilizing agents, wetting agents, emulsifying agents, sweetening agents, coloring agents, flavoring agents, salts for varying the osmotic pressure, buffers, coating agents and antioxidants. They can also contain still other therapeutically valuable substances. The formulations may conveniently be presented in unit dosage form and may be prepared by any methods known in the pharmaceutical art. Preferably, orlistat is administered according to the formulation shown in the Examples and in U.S. Pat. No. 6,004,996, respectively.

Preferred are the compounds of formula I and pharmaceutically acceptable salts thereof, particularly the compounds of formula I.

Further preferred are compounds according to formula I, wherein $R^1$ is phenyl or phenyl substituted with one to three substituents independently selected from alkoxy, alkyl, halogen and alkyl substituted with one to three halogen atoms. Particularly preferred are those compounds of formula I, wherein $R^1$ is phenyl or phenyl substituted with one or two substituents independently selected from alkoxy, alkyl, halogen and alkyl substituted with one to three halogen atoms.

Very preferred are the compounds of formula I, wherein $R^1$ is phenyl, dimethoxyphenyl, isopropyl-phenyl, fluoro-phenyl, chloro-phenyl, methyl-phenyl, trifluoromethyl-phenyl, methyl-fluoro-phenyl or isopropoxy-phenyl.

Another preferred embodiment of the present invention are the compounds of formula I, wherein $R^2$ is hydrogen, methyl or ethyl. Particularly preferred are those compounds, wherein $R^2$ is hydrogen or methyl. Very preferred are those compounds, wherein $R^2$ is methyl.

Also preferred are the compounds of formula I, wherein $R^3$ is methoxy or ethoxy. Particularly preferred is ethoxy.

Another preferred aspect of the present invention are the compounds of formula I, wherein $R^4$ is hydrogen.

Further preferred are those compounds of formula I, wherein the bond between the carbon atoms $C^a$ and $C^b$ is a carbon carbon double bond. These compounds have the following formula Ia

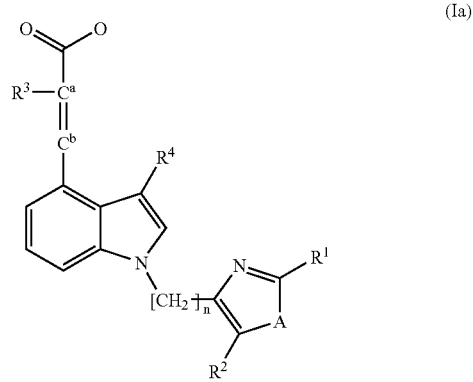

(Ia)

wherein $R^1$ to $R^4$, A and n are defined as before.

Particularly preferred are those compounds of formula I, wherein the bond between the carbon atoms $C^a$ and $C^b$ is a carbon carbon single bond. These compounds have the following formula Ib

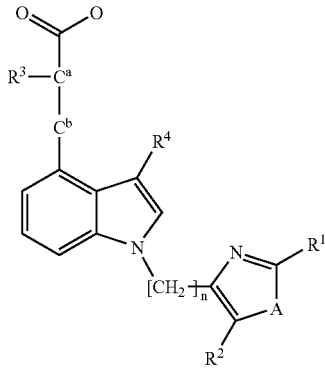
(Ib)

wherein $R^1$ to $R^4$, A and n are defined as before.

Preferred are compounds of formula I, wherein n is 1 or 2. Particularly preferred are those compounds, wherein n is 1 or 3. Further particularly preferred are those, wherein n is 1.

Also preferred are the compounds of formula I, wherein A is sulfur. Particularly preferred compounds of formula I are those, wherein A is oxygen.

The compounds of formula I can contain several asymmetric centres and can be present in the form of optically pure enantiomers, mixtures of enantiomers such as, for example racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbens or eluant).

The term "asymmetric carbon atom" means a carbon atom with four different substituents. According to the Cahn-Ingold-Prelog-Convention the asymmetric carbon atom can be of the "R" or "S" configuration.

Preferred are chiral compounds of formula (Ic),

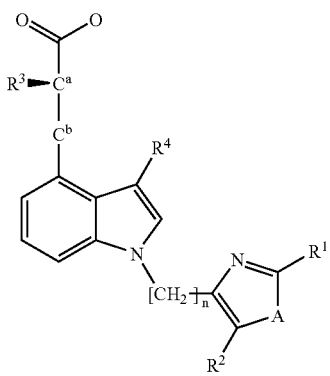
(Ic)

wherein $R^1$ to $R^4$, A and n are defined as before and the asymmetric carbon atom $C^a$ is of the R configuration.

Particularly preferred are chiral compounds of formula (Id),

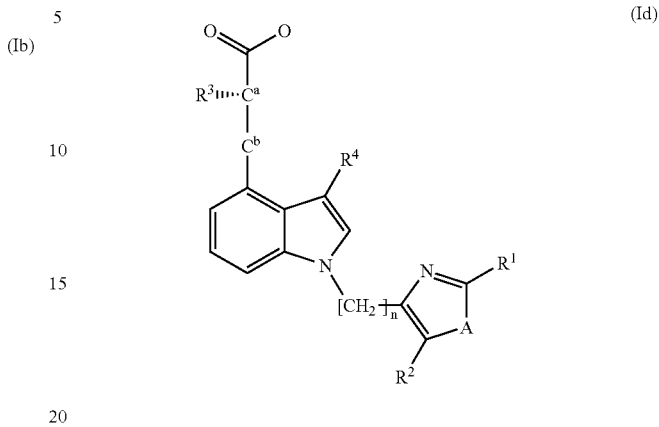
(Id)

wherein $R^1$ to $R^4$, A and n are defined as before and the asymmetric carbon atom $C^a$ is of the S configuration.

Examples of preferred compounds of formula (I) are
rac-3-{1-[2-(3,5-dimethoxy-phenyl)-5-methyl-oxazol-4-yl-methyl]-1H-indol-4-yl}-2-ethoxy-propionic acid;
rac-2-ethoxy-3-{1-[2-(4-isopropyl-phenyl)-5-methyl-oxazol-4-ylmethyl]-1H-indol-4-yl}-propionic acid;
rac-2-ethoxy-3-{1-[3-(5-methyl-2-phenyl-oxazol-4-yl)-propyl]-1H-indol-4-yl}-propionic acid;
rac-2-ethoxy-3-{1-[2-(5-methyl-2-phenyl-oxazol-4-yl)-ethyl]-1H-indol-4-yl}propionic acid;
rac-2-ethoxy-3-[1-(5-methyl-2-phenyl-oxazol-4-ylmethyl)-1H-indol-4-yl]-propionic acid;
rac-2-ethoxy-3-{1-[2-(2-fluoro-phenyl)-5-methyl-oxazol-4-ylmethyl]-1H-indol-4-yl}-propionic acid;
rac-3-{1-[2-(2-chloro-phenyl)-5-methyl-oxazol-4-ylmethyl]-1H-indol-4-yl}-2-ethoxy-propionic acid;
rac-2-ethoxy-3-[1-(5-methyl-2-o-tolyl-oxazol-4-ylmethyl)-1H-indol-4-yl]-propionic acid;
rac-3-{1-[2-(3-chloro-phenyl)-5-methyl-oxazol-4-ylmethyl]-1H-indol-4-yl}-2-ethoxy-propionic acid;
rac-2-ethoxy-3-{1-[5-methyl-2-(4-trifluoromethyl-phenyl)-oxazol-4-ylmethyl]-1H-indol-4-yl}-propionic acid;
rac-2-ethoxy-3-{1-[2-(4-fluoro-3-methyl-phenyl)-5-methyl-oxazol-4-ylmethyl]-1H-indol-4-yl}-propionic acid;
rac-2-ethoxy-3-{1-[2-(4-isopropoxy-phenyl)-5-methyl-oxazol-4-ylmethyl]-1H-indol-4-yl}-propionic acid and
rac-2-ethoxy-3-{1-[2-(4-isopropyl-phenyl)-thiazol-4-ylmethyl]-1H-indol-4-yl}-propionic acid.

Examples of particularly preferred compounds of formula (I) are
rac-3-{1-[2-(3,5-dimethoxy-phenyl)-5-methyl-oxazol-4-yl-methyl]-1H-indol-4-yl}-2-ethoxy-propionic acid;
rac-2-ethoxy-3-{1-[3-(5-methyl-2-phenyl-oxazol-4-yl)-propyl]-1H-indol-4-yl}-propionic acid and
rac-2-ethoxy-3-{1-[2-(4-fluoro-3-methyl-phenyl)-5-methyl-oxazol-4-ylmethyl]-1H-indol-4-yl}-propionic acid.

Processes for the manufacture of compounds of formula I are an object of the invention.

The substituents and indices used in the following description of the processes have the significance given above unless indicated to the contrary.

Compounds of general formula (I), wherein $R^1$ to $R^4$, A and n are defined as before can be prepared according to Scheme I:

Scheme I

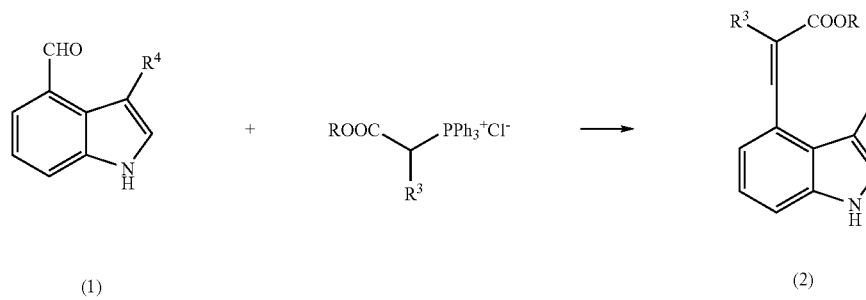

R = alkyl, aryl or aralkyl, preferably ethyl

X = halogen, CH₃SO₃

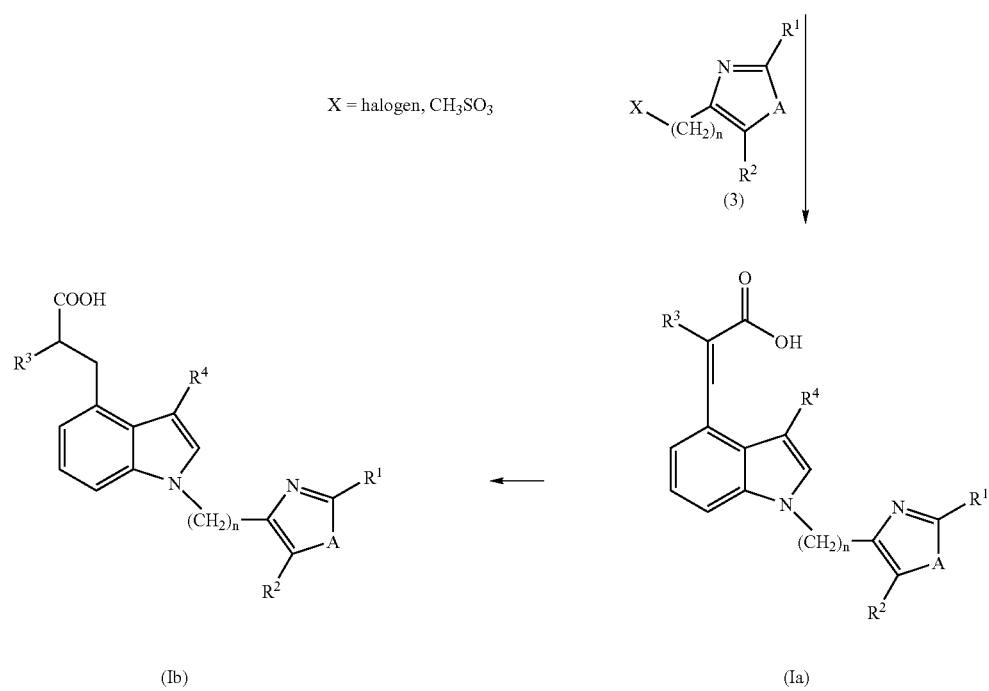

4-Formyl-indoles (1) can be reacted with a Wittig salt (Bach, Karen K.; El-Seedi, Hesham R.; Jensen, Henrik M.; Nielsen, Helene B.; Thomsen, Ib; Torssell, Kurt B. G; Tetrahedron (1994), 50(25), 7543–56) such as (1,2-diethoxy-2-oxoethyl)-triphenyl-phosphonium chloride or (1-methoxy-2-benzyloxy-oxoethyl)-triphenyl-phosphonium chloride in solvents like isopropanol, dichloromethane or tetrahydrofuran or mixtures thereof in the presence of a base like potassium carbonate or tetramethyl guanidine, preferably between 0° C. and the reflux temperature of the solvents, giving acrylic esters (2) as E and/or Z isomers.

Alkylation of (2) with the heterocycles (3) can be accomplished in a solvent like N,N-dimethylformamide in the presence of a base like sodium hydride or potassium tert-butylate, preferable between 0° C. and room temperature followed by hydrolysis of the ester function, preferably with lithium hydroxide in a solvent like dioxane preferable between 0° C. and room temperature. Alternatively, the alkylation with the heterocycles (3) can be accomplished with KOH in DMSO between 0° C. and 80° C., preferably at 22° C.; using these conditions, in situ hydrolysis to the corresponding acid is observed and the acrylic acids (Ia) can be obtained in a one step procedure.

Catalytic hydrogenation of (Ia) with palladium on charcoal in solvents like methanol, ethanol, dichloromethane or tetrahydrofuran or mixtures thereof leads to the indole propionic acids (Ib).

Alternatively, compounds of general formula (Ib), wherein R¹ to R⁴, A and n are defined as before can be prepared according to Scheme II:

Scheme II

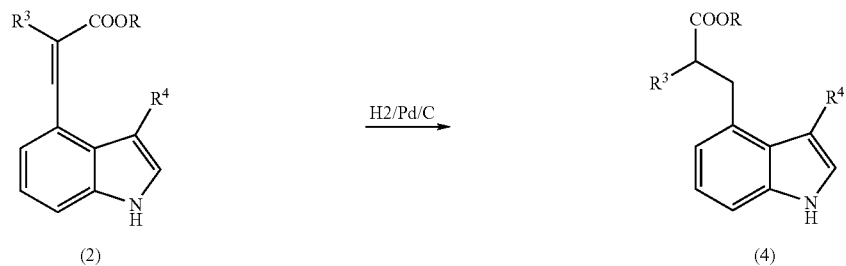

R = alkyl, aryl or aralkyl, preferably ethyl

X = halogen, CH$_3$SO$_3$

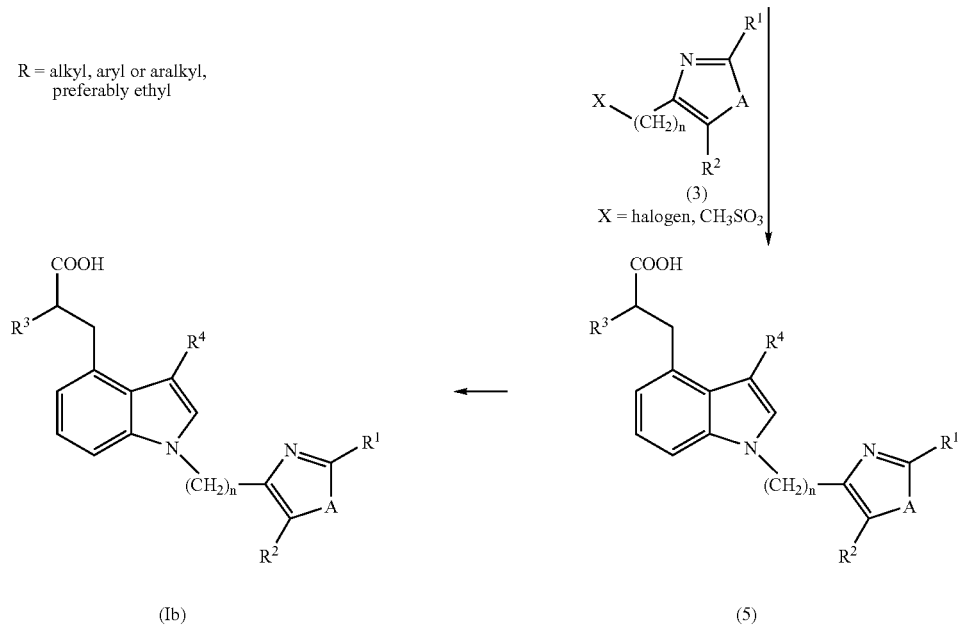

The alternative preparation of (Ib) according to Scheme II, preferentially be used when R$^3$ and R$^4$ are fixed and R$^1$, R$^2$ and A will be varied, follows the same type of reactions as described in Scheme I.

As alternative to the procedures described in Schemes I and II, compounds of general formula (Ib), particularly compounds wherein R$^3$ is varied, can be prepared according to Scheme III:

Scheme III

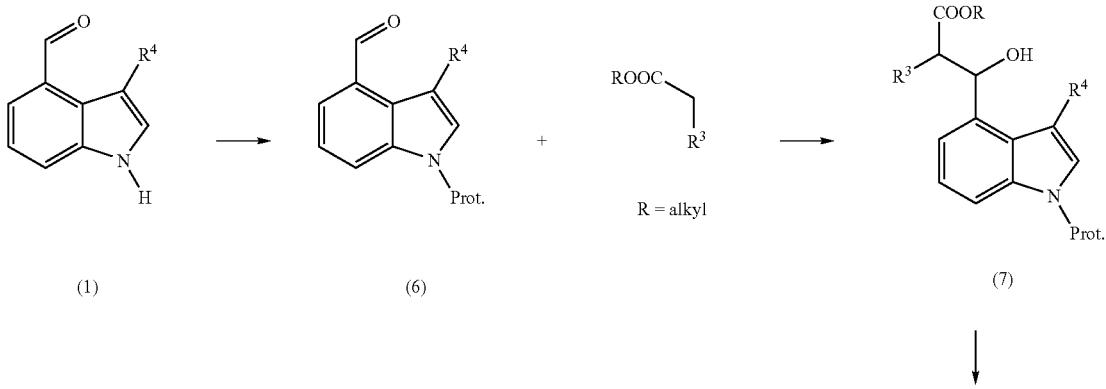

R = alkyl

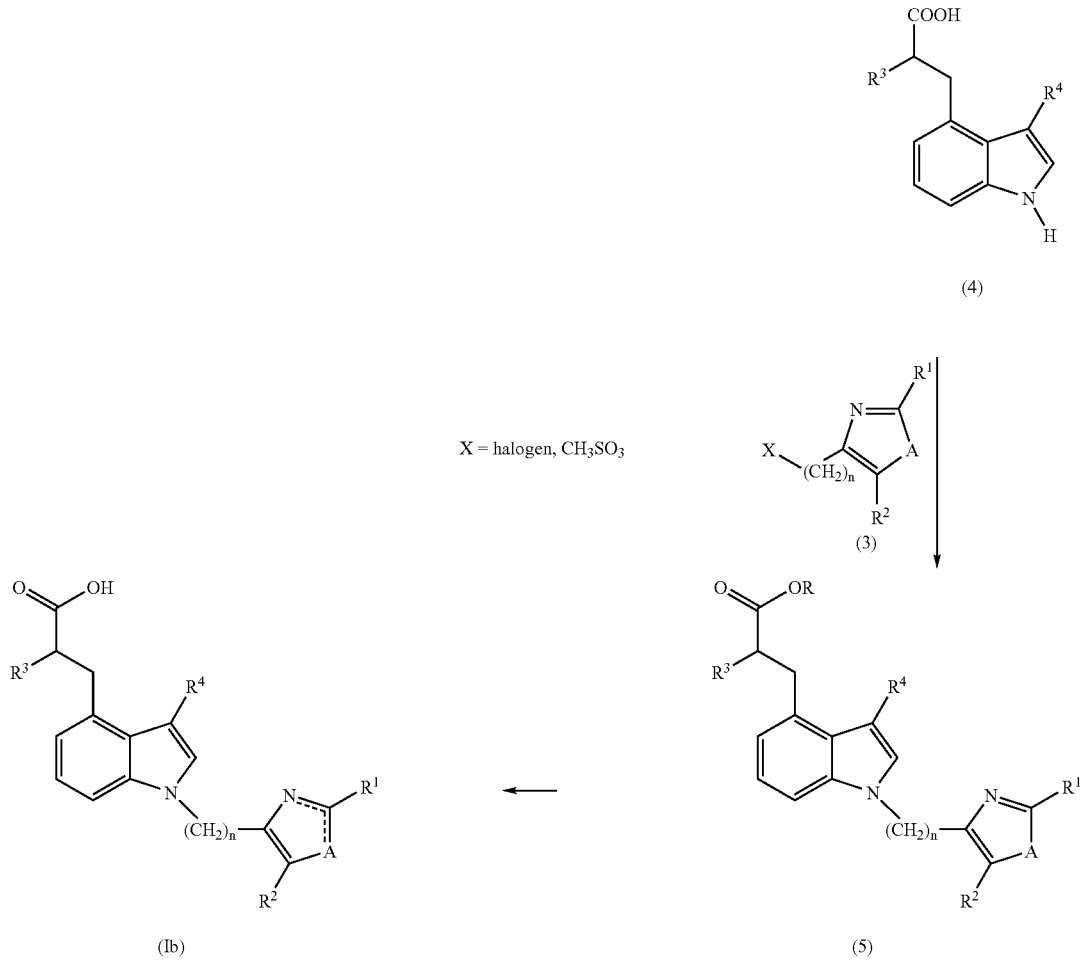

Formyl indoles (6) carrying a suitable protective function (Prot.) at the indole nitrogen group, e.g. a 2-trimethylsilanyl-ethoxymethyl (SEM)-group or a benzenesulfonyl group can react with enolates of alkoxy-acetic acid esters (preferably prepared at −78° C. in a solvent like tetrahydrofuran with a base like lithium diisopropylamide) at low temperature to give aldol compounds (7) as mixtures of diastereomeric racemates. Compounds (7) can be transformed into indole propionic acids (4) by different synthetic routes depending on the protective group used. If a benzenesulfonyl group is used as indole protective function, then, the following two step procedure is preferably used: i) elimination of water by treatment with para-toluenesulfonic acid in a solvent like benzene preferably at reflux; ii) reaction with magnesium in methanol at reflux to simultaneously reduce the double bond and remove the protective function. If a 2-trimethylsilanyl-ethoxymethyl (SEM)-group is used as indole protective function, then, the following five step procedure is preferably used: i) treatment with methanesulfonyl chloride in a solvent like dichloromethane followed by treatment with e.g. 1,8-diazabicyclo[5.4.0.]undec-7-ene(1,5,5) in a solvent like tetrahydrofuran preferably at elevated temperature to give the unsaturated ester compounds as mixtures of E and/or Z isomers; ii) hydrogenation of the double bond with e.g. palladium on charcoal in a solvent like ethanol; iii) saponification of the ester function using standard conditions; iv) removal of the protective function with e.g. tetra-butylammonium fluoride (as solution in tetrahydrofuran) in a solvent like N,N-dimethylformamide in the presence of ethylene diamine in a preferred temperature range between 50° C. and 80° C.; v) re-esterification using e.g. methyliodide, sodium hydrogen carbonate in N,N-dimethylformamide. The transformation of compounds (4) into ester compounds (5) by condensation with heterocycles (3) and subsequent saponification to compounds (Ig) can then be performed as outlined in Schemes I and II.

Homochiral acids (Ib) can be prepared by preparation of optically pure or optically enriched intermediates (e.g. by enzymatic resolution of the racemic esters (4) using e.g. a Lipase, the resolved acid being esterified after separation) and further transformation of such optically pure or optically enriched esters (4) into optically pure or optically enriched acids (Ib). Alternatively, racemic or optically enriched acids (Ib) can be separated into their antipodes by methods known in the art, such as separation of the antipodes via diastereomeric salts by crystallization with optically pure amines such as e.g. (R) or (S)-1-phenyl-ethylamine, (R) or (S)-1-naphthalen-1-yl-ethylamine, brucine, quinine or quinidine or by separation of the antipodes by specific chromatographic methods using either a chiral adsorbens or a chiral eluent.

4-Formyl-indoles (1) are known or can be synthesized by methods known in the art, e.g. from the corresponding 4-bromo- or 4-iodo-indoles: i) by treatment with copper (I) cyanide in quinoline at temperatures between 200° C. and 270° C. (compare Liebigs Ann. Chem. 1975, 160–194) followed by reduction of the nitriles thus formed with sodium hypophosphite and raney nickel preferably in a mixture of water, acetic acid and pyridine at temperatures ranging between room temperature and 60° C. [compare Helvetica Chimica Acta (1968) 51, 1616–1628] or ii) by treatment of the corresponding 4-bromo- or 4-iodo-indoles, which can optionally carry a protective function at the indole nitrogen atom, with an alkyl lithium reagent, e.g. n-butyl lithium, in a solvent like tetrahydrofuran preferably at −78° C. followed by treatment with N,N-dimethylformamide or N-formyl-piperidine.

4-Bromo- or 4-iodo-indoles, which can optionally carry a protective function at the indole nitrogen atom, are known or can be synthesized by methods known in the art; possible syntheses of 4-bromo- or 4-iodo-indoles are described in Chemistry-A European Journal (2002), 8(9), 2034–2046 and in Tetrahedron Letters (2001), 42(6), 983–985.

Starting compounds of formula (3), wherein A is oxygen and n is 1 or 2 can be obtained e.g. according to Scheme IV.

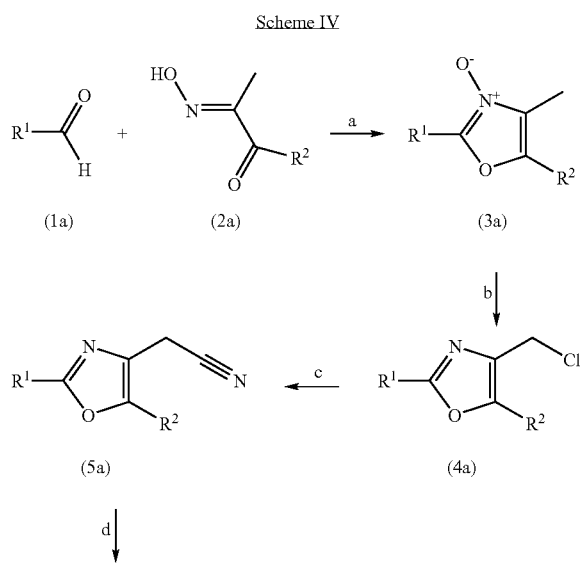

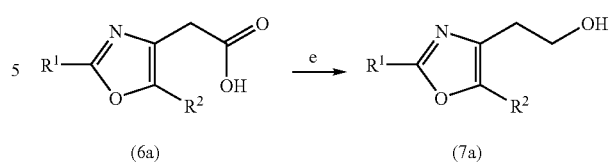

Aldehydes (1a) are commercially available and described in the literature. They are condensed with diketo-monoximes (2a) according to literature precedence (Goto) Y.; Yamazaki) M.; Hamana, M.; Chem Pharm Bull (1971), 19, 2050) in the presence of a strong acid, typically HCl, in a polar solvent like AcOH to yield the oxazole-N-oxides (3a) (step a). Subsequent treatment with $POCl_3$ in dichloromethane under reflux provides the corresponding primary chlorides (4a) (Goto, Y.; Yamazaki, M.; Hamana, M.; Chem Pharm Bull (1971), 19, 2050, step b). These intermediates are either used as such, transformed according to well established methods into the corresponding alcohols or activated alcohols like mesylates or tosylates or into the bromides or iodides, or finally further elaborated via $S_N2$-reaction with NaCN to give, via nitrils (5a) (step c), exhaustive hydrolysis (step d) and reduction (step e), e.g. with borane in tetrahydrofuran, the building blocks (7a). Finally, the alcohols (7a) can be converted into compounds of formula (3) e.g by treatment with methanesulfonyl chloride in dichloromethane in.the presence of a base like triethylamine preferably in a temperature range between −20° C. and room temperature or by reaction with carbon tetrachloride or carbon tetrabromide and triphenylphosphine in solvents like tetrahydrofuran preferably in a temperature range between room temperature and the reflux temperature of the solvents; thus yielding compounds of formula (3) as methanesulfonates, chlorides or bromides, respectively.

4-Chloromethyl-2-aryl or 2-heteroaryl-oxazoles (4a) with $R^2$ equal hydrogen are preferably prepared from the corresponding aryl or heteroaryl carboxamides and 1,3-dichloro-acetone as described e.g. in Bioorg. Med. Chem. Lett. (2000), 10(17), 2041–2044.

Starting compounds of formula (3), wherein A is oxygen and n is 3 can be obtained e.g. according to Scheme V:

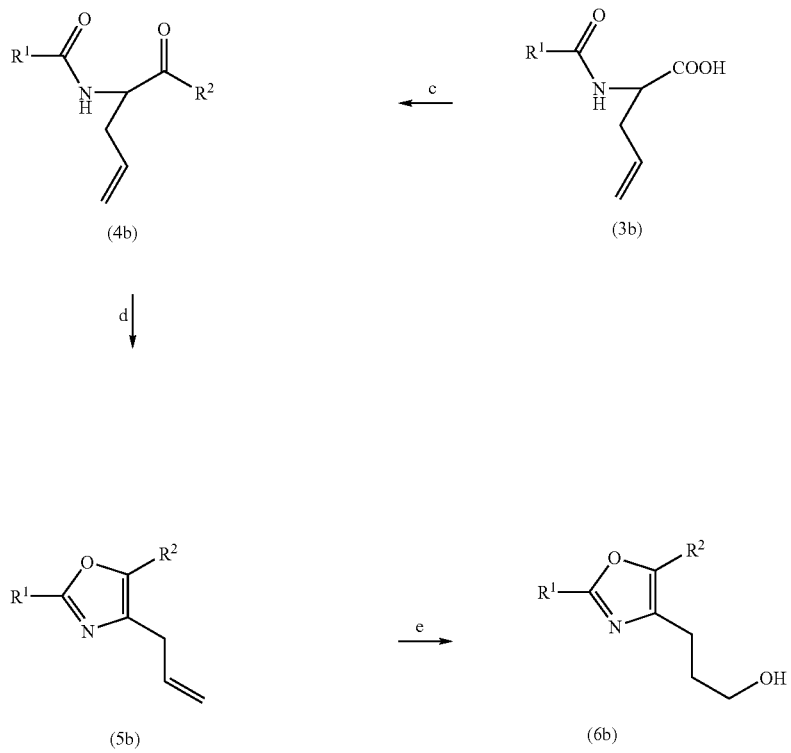

N-Acyl-glycine esters (1b) are either commercially available, known, or can be prepared by standard operations of N-acylation. Mono-allylated esters (2b) can easily be obtained by double deprotonation of (1b) with a strong, non-nucleophilic base like LiHMDS in an aprotic solvent like THF, typically at −78° C., followed by treatment with allyl bromide to produce selectively the C-alkylated products (2b) (step a). Standard hydrolysis generates intermediate acids (3b) (step b), which are then transformed, following well established literature precedence (J. Med. Chem. (1996), 39, 3897), into compounds (4b) (step c). Ring-closure to the oxazole using trifluoro-acetic acid and trifluoro-acetic anhydride as reagents generates key intermediates (5b) (step d), which, finally, are elaborated via hydroboration to the target alcohols (6b), e.g. with 9-BBN in THF and ensuing oxidative work-up with $H_2O_2$ and NaOH (step e). Finally, the alcohols (6b) can be converted into compounds of formula (3) e.g by treatment with methanesulfonyl chloride in dichloromethane in the presence of a base like triethylamine preferably in a temperature range between −20° C. and room temperature or by reaction with carbon tetrachloride or carbon tetrabromide and triphenylphosphine in solvents like tetrahydrofuran preferably in a temperature range between room temperature and the reflux temperature of the solvents; thus yielding compounds of formula (3) as methanesulfonates, chlorides or bromides, respectively.

Starting compounds of formula (3), wherein A is sulfur and n is 1 can be obtained e.g. according to Scheme VI:

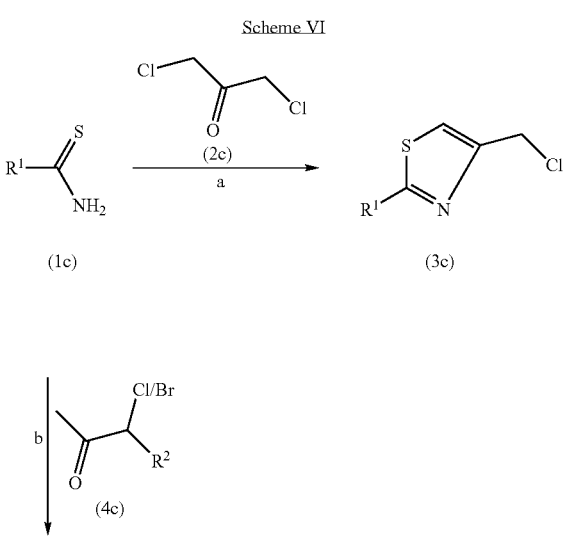

-continued

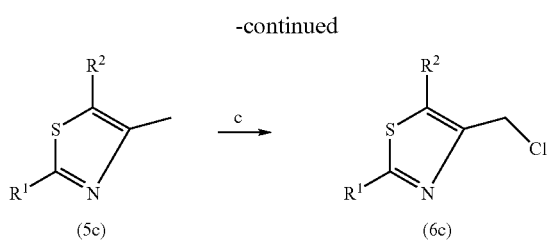

Thioamides (1c) are known or can be prepared by methods known in the art, e.g. by treatment of the corresponding carboxamide with phosphorus pentasulfide or with Lawesson's Reagent [2,4-bis(4-methoxyphenyl)-1,3-dithia-2,4-diphosphetane-2,4-disulfide] in a solvent like toluene at temperatures preferably between 60° C. and the reflux temperature of the solvent. Thioamides (1c) may be condensed with 1,3-dichloroacetone in solvents like acetone or acetonitrile between room temperature and the reflux temperature of the solvents, followed by treatment with strong acid, e.g. concentrated sulfuric acid, preferably at ambient temperature (step a). Alternatively, thioamides (1c) are condensed with alpha-bromo or alpha-chloro ketones (4c) in a solvent like ethanol, preferably at reflux temperature, to give aryl-thiazoles (5c) bearing a methyl function at position 4 (step b) [compare Eur. Pat. Appl. (1987), EP 207453 A2]. By treatment of these aryl-thiazoles (5c) with N-chlorosuccinimide in solvents like acetonitrile, preferably at reflux temperature, chloromethyl compounds (6c) are obtained (step c) [compare PCT Int. Appl. (2001), WO 0119805 A1].

Starting compounds of formula (3), wherein A is sulfur and n is 2 or 3 can be obtained e.g. according to Scheme VII:

Condensation of thioamides (id) with a suitable bis-electrophile, e.g. methyl 4-bromo- or 4-chloro-3-oxo-alkanoates (2d), preferably in a solvent like toluene at elevated temperatures (e.g. at reflux temperature), gives thiazoles (3d) carrying an acetic acid ester function at position 4 (step a) [compare PCT Int. Appl. (1997), WO97/31907 A1]. 4-Bromo-3-oxo-alkanoates (2d) are known or can be prepared by methods known in the art [compare PCT Int. Appl. (2001), WO 01/79202 A1]. Thiazoles (3d) can then be reduced, e.g. with lithium aluminum hydride, to thiazoles (4d) (step b). Optionally, an elongation of the side chain can then be performed by standard methods, such as transformation of the alcohol function into a leaving group, e.g. a mesylate, ensuing treatment with cyanide, saponification and reduction, affording thiazoles (5d) with a hydroxypropyl function attached to position 4 (step c). Finally, the alcohols (4d) and (5d) can be activated to the mesylates or tosylates using well known standard procedures.

The conversion of a compound of formula I into a pharmaceutically acceptable salt can be carried out by treatment of such a compound with an inorganic acid, for example a hydrohalic acid, such as, for example, hydrochloric acid or hydrobromic acid, sulfuric acid, nitric acid, phosphoric acid etc., or with an organic acid, such as, for example, acetic acid, citric acid, maleic acid, fumaric acid, tartaric acid, methanesulfonic acid or p-toluenesulfonic acid. The corresponding carboxylate salts can also be prepared from the compounds of formula I by treatment with physiologically compatible bases such as sodium or potassium hydroxide or a tertiary amine as triethylamine.

The conversion of compounds of formula I into pharmaceutically acceptable esters or amides can be carried out e.g. by treatment of suited amino or hydroxyl groups present in the molecules with an carboxylic acid such as acetic acid, with a condensating reagent such as benzotriazol-1-yloxytris(dimethylamino)phosphonium hexafluorophosphate (BOP)

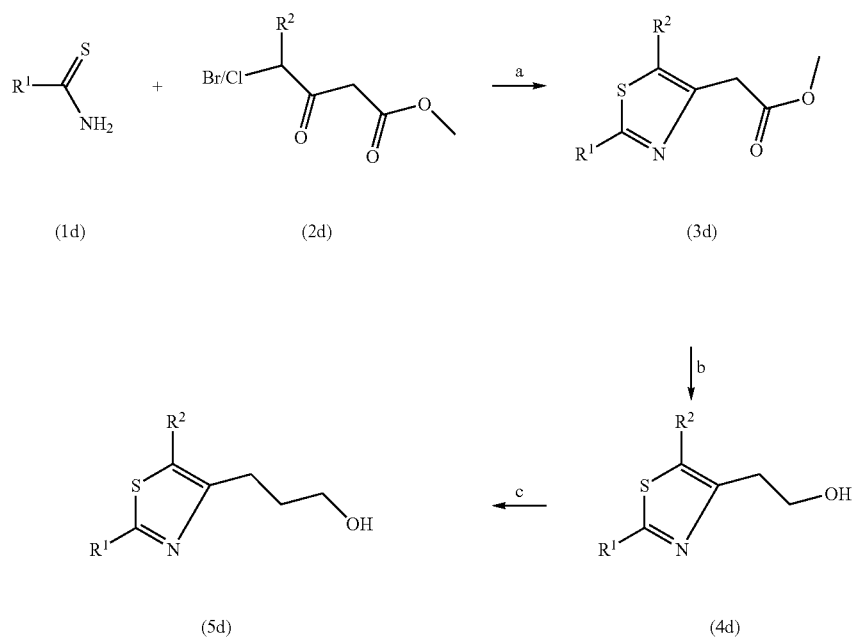

or N,N-dicylohexylcarbodiimide (DCCI) to produce the carboxylic ester or carboxylic amide.

Preferably, the conversion of compounds of formula I into pharmaceutically acceptable esters can e.g. be carried out by treatment of compounds of formula (I) in the presence of a condensating reagent such as benzotriazol-1-yloxytris(dimethylamino)phosphonium hexafluorophosphate (BOP) or N,N-dicylohexylcarbodiimide (DCCI) and 4-dimethylamino-pyridine with the corresponding alcohol in solvents such as e.g. N,N-dimethylformamide according to methods well known in the art.

Further preferred is a process for the preparation of a compound according to formula I comprising one of the following reactions:

reaction of a compound according to formula

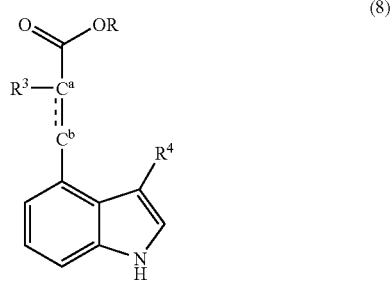
(8)

in the presence of a compound according to formula

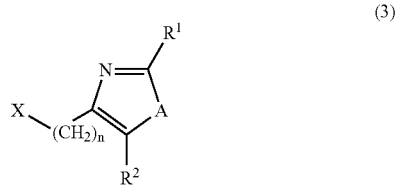
(3)

wherein $R^1$ to $R^4$, A and n are defined as before, X is halogen or $CH_3SO_3$, R is alkyl, aryl or aralkyl and, wherein the bond between the carbon atoms $C^a$ and $C^b$ is a carbon carbon single or double bond;

b) hydrogenation of a compound according to formula

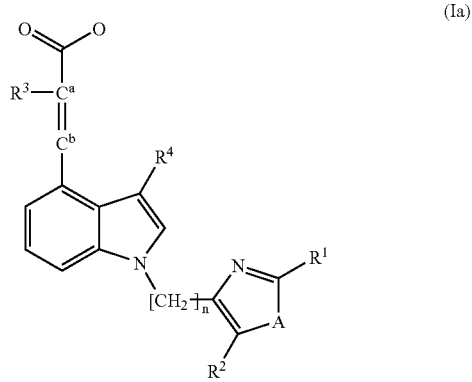
(Ia)

wherein $R^1$ to $R^4$, A and n are defined as before.

Preferred intermediates are:
(Z)-2-ethoxy-3-(1H-indol-4-yl)-acrylic acid ethyl ester;
rac-2-ethoxy-3-(1H-indol-4-yl)-propionic acid ethyl ester.

As described above, the compounds of formula (I) of the present invention can be used as medicaments for the treatment and/or prevention of diseases which are modulated by PPARα and/or PPARγ agonists. Examples of such diseases are diabetes, particularly non-insulin dependent diabetes mellitus, elevated blood pressure, increased lipid and cholesterol levels, atherosclerotic diseases, metabolic syndrome, endothelial dysfunction, procoagulant state, dyslipidemia, polycystic ovary syndrome, inflammatory diseases (such as e.g. crown disease, inflammatory bowel disease, collitis, pancreatitis, cholestasis/fibrosis of the liver, and diseases that have an inflammatory component such as e.g. Alzheimer's disease or impaired/improvable cognitive function) and proliferative diseases (cancers such as e.g. liposarcoma, colon cancer, prostate cancer, pancreatic cancer and breast cancer). The use as medicament for the treatment and/or prevention of non-insulin dependent diabetes mellitus is preferred.

The compounds of formula I described above for use as therapeutically active substances are a further object of the invention. Preferred is the use as therapeutically active substances for the prophylaxis and/or therapy of diabetes, non-insulin dependent diabetes mellitus, elevated blood pressure, increased lipid and cholesterol levels, atherosclerotic diseases or metabolic syndrome and particularly preferred non-insulin dependent diabetes mellitus.

Also an object of the invention are compounds described above for the preparation of medicaments for the prophylaxis and/or therapy of diseases which are modulated by PPARα and/or PPARγ agonists, preferably for the production of medicaments for the prophylaxis and/or therapy of diabetes, non-insulin dependent diabetes mellitus, elevated blood pressure, increased lipid and cholesterol levels, atherosclerotic diseases or metabolic syndrome and particularly preferred non-insulin dependent diabetes mellitus.

Likewise an object of the invention are pharmaceutical compositions comprising a compound of formula I described above and a therapeutically inert carrier. Another object of the present invention is the above pharmaceutical composition further comprising a therapeutically effective amount of a lipase inhibitor particularly, wherein the lipase inhibitor is orlistat.

An object of the invention is also the use of the compounds described above for the production of medicaments, particularly for the treatment and/or prophylaxis of diseases which are modulated by PPARα and/or PPARγ agonists, preferably diabetes, non-insulin dependent diabetes mellitus, elevated blood pressure, increased lipid and cholesterol levels, atherosclerotic diseases or metabolic syndrome and particularly preferred non-insulin dependent diabetes mellitus.

A further object of the present invention is the use of a compound of formula I in the manufacture of a medicament for the treatment and/or prophylaxis of diseases which are modulated by PPARα and/or PPARγ agonists in a patient who is also receiving treatment with a lipase inhibitor. Preferred is the above use, wherein the lipase inhibitor is orlistat. Particularly preferred is the above use for the treatment and/or prophylaxis of diseases, wherein the diseases are diabetes, non-insulin dependent diabetes mellitus, elevated blood pressure, increased lipid and cholesterol levels, atherosclerotic diseases or metabolic syndrome and particularly preferred non-insulin dependent diabetes mellitus.

A further object of the invention comprises compounds which are manufactured according to one of the described processes.

A further object of the invention is a method for the treatment and/or prophylaxis of diseases which are modulated by PPARα and/or PPARγ agonists, preferably diabetes, non-insulin dependent diabetes mellitus, elevated blood pressure, increased lipid and cholesterol levels, atherosclerotic diseases or metabolic syndrome and particularly preferred non-insulin dependent diabetes mellitus, whereby an effective amount of a compound of formula I is administered. Another object of the present invention is the above method which further comprises administration to the human a therapeutically effective amount of a lipase inhibitor, particularly, wherein the lipase inhibitor is orlistat. The above method for simultaneous, separate or sequential administration is also an object of the present invention.

Assay Procedures

The following tests can be used in order to determine the activity of the compounds of formula I.

Background information on the performed assays can be found in: Nichols J S et al. "Development of a scintillation proximity assay for peroxisome proliferator-activated receptor gamma ligand binding domain", (1998) Anal. Biochem. 257: 112–119.

Full-length cDNA clones for human PPARα and mouse PPARγ were obtained by RT-PCR from human adipose and mouse liver cRNA, respectively, cloned into plasmid vectors and verified by DNA sequencing. Bacterial and mammalian expression vectors were constructed to produce glutathione-s-transferase (GST) and Gal4 DNA binding domain proteins fused to the ligand binding domains (LBD) of PPARγ (aa 174 to 476) and PPARα (aa 167 to 469). To accomplish this, the portions of the cloned sequences encoding the LBDs were amplified from the full-length clones by PCR and then subcloned into the plasmid vectors. Final clones were verified by DNA sequence analysis.

Induction, expression, and purification of GST-LBD fusion proteins were performed in *E. coli* strain BL21 (pLysS) cells by standard methods (Ref: Current Protocols in Molecular Biology, Wiley Press, edited by Ausubel et al.).

Radioligand Binding Assay

PPARα receptor binding was assayed in TKE10 (10 mM Tris-HCl, pH 8, 50 mM KCl, 2 mM EDTA, 0.1 mg/ml fatty acid free BSA and 10 mM DTT). For each 96 well 2.4 ug equivalent of GST-PPARα-LBD fusion protein and radioligand, e.g. 40000 dpm 2(S)-(2-benzoyl-phenylamino)-3-{4-[1,1-ditritio-2-(5-methyl-2-phenyl-oxazol-4-yl) -ethoxy]-phenyl}-propionic acid, were incubated in 100 ul volume at RT for 2 hrs. Bound ligand was removed from unbound ligand by solid phase separation using MultiScreen plates (Millipore) filled with 80 ul of SG25 according to the manufacturer's recommendations.

PPARγ receptor binding was assayed in TKE50 (50 mM Tris-HCl, pH 8, 50 mM KCl, 2 mM EDTA, 0.1 mg/ml fatty acid-free BSA and 10 mM DTT). For each 96 well reaction an 140 ng equivalent of GST-PPARγ-LBD fusion protein was bound to 10 ug SPA beads (PharmaciaAmersham) in a final volume of 50 ul by shaking. The resulting slurry was incubated for 1 h at RT and centrifuged for 2 min at 1300 g. The supernatant containing unbound protein was removed and the semidry pellet containig the recptor-coated beads was resolved in 50 ul of TKE. For radioligand binding e.g. 10000 dpm 2(S)-(2-benzoyl-phenylamino)-3-{4-[1,1-ditritio-2-(5-methyl-2-phenyl-oxazol-4-yl) -ethoxy]-phenyl}-propionic acid in 50 ul were added, the reaction incubated at RT for 1 h and scintillation proximity counting performed. All binding assays were performed in 96 well plates and the amount of bound ligand measured on a Packard TopCount using OptiPlates (Packard). Nonspecific binding was determined in the presence of $10^{-4}$ M unlabelled compound. Dose response curves were done in triplicates within a range of concentration from $10^{-10}$ M to $10^{-4}$ M.

Luciferase Transcriptional Reporter Gene Assays

Baby hamster kidney cells (BHK21 ATCC CCL10) were grown in DMEM medium containing 10% FBS at 37° C. in a 95% $O_2$:5% $CO_2$ atmosphere. Cells were seeded in 6 well plates at a density of $10^5$ Cells/well and then batch-transfected with either the pFA-PPARγ-LBD or pFA-PPARα-LBD expression plasmids plus the pFR-luc reporter plasmid and an expression plasmid encoding the secretable form of alkaline phosphatase (SEAP) as a normalization control. Transfection was accomplished with the Fugene 6 reagent (Roche Molecular Biochemicals) according to the suggested protocol. Six hours following transfection, the cells were harvested by trypsinization and seeded in 96 well plates at a density of $10^4$ cells/well. After 24 hours to allow attachment of cells, the medium was removed and replaced with 100 ul of phenol red-free medium containing the test substances or control ligands (final. 0.1% DMSO). Following incubation of the cells for 24 hours with substances, 50 ul of the supernatant was recovered and analyzed for SEAP activity (Roche Molecular Biochemicals). The remainder of the supernatant was discarded, 50 ul PBS was added per well followed by one volume of Luciferase Constant-Light Reagent (Roche Molecular Biochemicals) to lyse the cells and initiate the luciferase reaction. Luminescence for both SEAP and luciferase was measured in a Packard TopCount. Luciferase activity was normalized to the SEAP control and transcriptional activation in the presence of a test substance was expressed as fold-activation over cells incubated in the absence of the substance. EC50 values were calculated using the XLfit program (ID Business Solutions Ltd. UK).

The compounds of the present invention exhibit IC50 values below 50 μM for PPARα and PPARγ. Preferred compounds have IC50 values below 10 μM, particularly below 3500 nM for PPARα and PPARγ. Very preferred compounds have IC50 values below 1000 nM for PPARα and PPARγ.

The compounds of the invention exhibit EC50 values below 50 μM for PPARα and PPARγ. Preferred compounds exhibits EC50 values below 10 μM, particularly preferred below 3500 nM for PPARα and PPARγ. Very preferred compounds have EC50 values below 1000 nM for PPARα and PPARγ.

The following table shows measured values for some selected compounds of the present invention and for a compound already known in the art (e.g.: Rosiglitazone, Drugs 1999, Vol 57(6), 921–930).

|  | PPARγ $IC_{50}$ (μM) | PPARα $EC_{50}$ (μM) | PPARγ $EC_{50}$ (μM) |
| --- | --- | --- | --- |
| Example 1 | 0.068 | 0.008 | 0.007 |
| Example 2 | 0.053 | 0.20 | 0.093 |
| Example 3 | 0.27 | 0.19 | 0.090 |
| Example 10 | 1.4 | 0.044 | 0.14 |
| Rosiglitazone | 1090 nmol/l | inactive | 405 nmol/l |

The compounds of formula I and their pharmaceutically acceptable salts and esters can be used as medicaments, e.g. in the form of pharmaceutical preparations for enteral, parenteral or topical administration. They can be administered, for example, perorally, e.g. in the form of tablets, coated tablets, dragees, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula I and their pharmaceutically acceptable, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragees and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 0.1 mg to about 1000 mg, especially about 0.1 mg to about 100 mg, comes into consideration. Further preferred daily dosages for adult patients are of about 1 mg to about 1000 mg, especially about 1 mg to about 100 mg. Depending on the dosage it is convenient to administer the daily dosage in several dosage units.

The pharmaceutical preparations conveniently contain about 0.05–500 mg, particularly 0.5–500 mg, preferably 0.5–100 mg, of a compound of formula I.

The following Examples serve to illustrate the present invention in more detail. They are, however, not intended to limit its scope in any manner.

EXAMPLES

A: Preparation of Intermediates rac-2-Ethoxy-3-(1H-indol-4-yl)-propionic acid ethyl ester (Z) -2-Ethoxy-3-(1H-indol-4-yl)-acrylic acid ethyl ester To a solution of 35.01 g (81.6 mmol) of (1,2-diethoxy-2-oxoethyl)triphenyl phosphonium chloride in 200 ml of dichloromethane was added at 0° C. 11.01 ml (87.1 mmol) of tetramethyl guanidine and the mixture was warmed to 22° C. The mixture was treated with 7.9 g (54.4 mmol) of 4-formyl-indole and stirring was continued at 40° C. for 16 h. The mixture was treated again with 10.0 g (23.3 mmol) of the Wittig salt and 8.0 ml (24.0 mmol) of tetramethyl guanidine and stirring was continued at 40° C. for 24 h after which time the conversion was complete. The reaction mixture was poured into crashed ice and then extracted twice with $MeCl_2$. The organic layer was washed with water, dried over $MgSO_4$, filtered and evaporated. The residue was chromatographed on silica (n-heptane/AcOEt, 95:5 to 4:1) to give 15.12 g of the title compound as a light yellow solid.

MS: 259.1 ($M^+$).

rac-2-Ethoxy-3-(1H-indol-4-yl)-propionic acid ethyl ester

A suspension of 15.0 g of (Z)-2-ethoxy-3-(1H-indol-4-yl)-acrylic acid ethyl ester in 250 ml of EtOH and 3.08 g of Pd/C (10%) was hydrogenated at 22° C. for 2 h, after which time hydrogen uptake ceased. The suspension was filtered, the filtrate evaporated and the residue chromatographed on silica gel (eluent: gradient of hexane and ethyl acetate) to give 12.28 g of the title compound as a light brown oil.

MS: 279.2 $(M+NH_4)^+$.

B: Preparation of Final Compounds

Example 1 a] rac-3-{1-[2-(3,5-Dimethoxy-phenyl)-5-methyl-oxazol-4-ylmethyl]-1H-indol-4-yl}-2-ethoxy-propionic acid ethyl ester 0.048 g (1.10 mmol) Sodium hydride (55% in mineral oil) was added in one portion below 5° C. and under argon to a stirred solution of 0.261 g (1.00 mmol) rac-2-ethoxy-3-(1H-indol-4-yl)-propionic acid ethyl ester and 0.321 g (1.20 mmol) 4-chloromethyl-2-(3,5-dimethoxy-phenyl)-5-methyl-oxazole in 15.0 ml N,N-dimethylformamide. The reaction mixture was warmed up to room temperature and then stirred for 16 hours at ambient temperature. It was then diluted with cold water and extracted two times with ethyl acetate. The combined organic phases were dried over $MgSO_4$, filtered and evaporated. The residue formed was purified by flash-chromatography (silica gel; eluent: gradient of hexane and ethyl acetate) to give 0.413 g (84%) rac-3-{1-[2-(3,5-dimethoxy-phenyl)-5-methyl-oxazol-4-yl-methyl]-1H-indol-4-yl}-2-ethoxy-propionic acid ethyl ester as light yellow solid.

MS: 493.3 $(M+H)^+$.

b] rac-3-{1-[2-(3,5-Dimethoxy-phenyl)-5-methyl-oxazol-4-ylmethyl]-1H-indol-4-yl}-2-ethoxy-propionic acid rac-3-{1-[2-(3,5-Dimethoxy-phenyl)-5-methyl-oxazol-4-ylmethyl]-1H-indol-4-yl}-2-ethoxy-propionic acid ethyl ester (0.390 g, 0.79 mmol ) was dissolved in 15 ml of dioxane; 1.98 ml of an aqueous solution of LiOH (1.0 molar, 1.98 mmol) were then added at room temperature. The resulting mixture was stirred overnight at room temperature and then poured onto ice, neutralized to pH 4 with HCl (1N) and extracted 3 times with $MeCl_2$. The combined organic phases were washed with water, dried over magnesium sulfate, filtered and evaporated to give 0.242 g (66 %) of rac-3-{1-[2-(3,5-dimethoxy-phenyl)-5-methyl-oxazol-4-yl-methyl]-1H-indol-4-yl}-2-ethoxy-propionic acid as light yellow solid.

MS: 465.3 $(M+H)^+$.

Example 2 rac-2-Ethoxy-3-{1-[2-(4-isopropyl-phenyl)-5-methyl-oxazol-4-ylmethyl]-1H-indol-4-yl}-propionic acid In analogy to the procedures described in examples 1 a] and 1 b], rac-2-ethoxy-3-(1H-indol-4-yl)-propionic acid ethyl ester was reacted with 4-chloromethyl-2-(4-isopropyl-phenyl)-5-methyl-oxazole in N,N-dimethylformamide in the presence of sodium hydride to yield rac-3-{1-[2-(4-isopropyl-phenyl)-5-methyl-oxazol-4-ylmethyl]-1H-indol-4-yl}-2-ethoxy-propionic acid ethyl ester, which was subsequently saponified to yield rac-3-{1-[2-(4-isopropyl-phenyl)-5-methyl-oxazol-4-ylmethyl]-1H-indol-4-yl}-2-ethoxy-propionic acid as light green solid.

MS: 447.3 $(M+H)^+$.

Example 3 rac-2-Ethoxy-3-{1-[3-(5-methyl-2-phenyl-oxazol-4-yl)-propyl]-1H-indol-4-yl}-propionic acid In analogy to the procedures described in examples 1 a] and 1 b], rac-2-ethoxy-3-(1H-indol-4-yl)-propionic acid ethyl ester was reacted with methanesulfonic acid 3-(5-methyl-2-phenyl-oxazol-4-yl)-propyl ester in N,N-dimethylformamide in the presence of sodium hydride to yield rac-2-ethoxy-3-{1-[3-(5-methyl-2-phenyl-oxazol-4-yl)-propyl]-1H-indol-4-yl}-propionic acid ethyl ester, which was subsequently saponified to yield rac-2-ethoxy-3-{1-[3-(5-methyl-2-phenyl-oxazol-4-yl)-propyl]-1H-indol-4-yl}-propionic acid as light brown oil.

MS: 433.4 $(M+H)^+$.

Example 4 rac-2-Ethoxy-3-{1-[2-(5-methyl-2-phenyl-oxazol-4-yl)-ethyl]-1H-indol-4-yl}-propionic acid In analogy to the procedures described in examples 1 a] and 1 b], rac-2-ethoxy-3-(1H-indol-4-yl)-propionic acid ethyl ester was reacted with methanesulfonic acid 2-(5-methyl-2-phenyl-oxazol-4-yl)-ethyl ester in N,N-dimethylformamide in the presence of sodium hydride to yield rac-2-ethoxy-3-{1-[2-(5-methyl-2-phenyl-oxazol-4-yl)-ethyl]-1H-indol-4-yl}-propionic acid ethyl ester, which was subsequently saponified to yield rac-2-ethoxy-3-{1-[2-(5-methyl-2-phenyl-oxazol-4-yl)-ethyl]-1H-indol-4-yl}-propionic acid as light yellow solid.

MS: 417.3 $(M-H)^-$.

Example 5 rac-2-Ethoxy-3-[1-(5-methyl-2-phenyl-oxazol-4-ylmethyl)-1H-indol-4-yl]-propionic acid In analogy to the procedures described in examples 1 a] and 1 b], rac-2-ethoxy-3-(1H-indol-4-yl)-propionic acid ethyl ester was reacted with 4-chloromethyl-5-methyl-2-phenyl-oxazole in N,N-dimethylformamide in the presence of sodium hydride to yield rac-2-ethoxy-3-[1-(5-methyl-2-phenyl-oxazol-4-ylmethyl)-1H-indol-4-yl]-propionic acid ethyl ester, which was subsequently saponified to yield rac-2-ethoxy-3-[1-(5-methyl-2-phenyl-oxazol-4-ylmethyl)-1H-indol-4-yl]-propionic acid as off-white solid.

MS: 403.3 $(M-H)^-$.

Example 6 rac-2-Ethoxy-3-{1-[2-(2-fluoro-phenyl)-5-methyl-oxazol-4-ylmethyl]-1H-indol-4-yl}-propionic acid In analogy to the procedures described in examples 1 a] and 1 b], rac-2-ethoxy-3-(1H-indol-4-yl)-propionic acid ethyl ester was reacted with 4-chloromethyl-2-(2-fluoro-phenyl)-5-methyl-oxazole in N,N-dimethylformamide in the presence of sodium hydride to yield rac-2-ethoxy-3-{1-[2-(2-fluoro-phenyl)-5-methyl-oxazol-4-ylmethyl]-1H-indol-4-yl}-propionic acid ethyl ester, which was subsequently saponified to yield rac-2-ethoxy-3-{1-[2-(2-fluoro-phenyl)-5-methyl-oxazol-4-ylmethyl]-1H-indol-4-yl}-propionic acid as off-white solid.

MS: 421.2 $(M-H)^-$.

Example 7 rac-3-{1-[2-(2-Chloro-phenyl)-5-methyl-oxazol-4-ylmethyl]-1H-indol-4-yl}-2-ethoxy-propionic acid In analogy to the procedures described in examples 1 a] and 1 b], rac-2-ethoxy-3-(1H-indol-4-yl)-propionic acid ethyl ester was reacted with 4-chloromethyl-2-(2-chloro-phenyl)-5-methyl-oxazole in N,N-dimethylformamide in the presence of sodium hydride to yield rac-3-{1-[2-(2-chloro-phenyl)-5-methyl-oxazol-4-ylmethyl]-1H-indol-4-yl}-2-ethoxy-propionic acid ethyl ester, which was subsequently saponified to yield rac-3-{1-[2-(2-chloro-phenyl)-5-methyl-oxazol-4-ylmethyl]-1H-indol-4-yl}-2-ethoxy-propionic acid as light brown solid.

MS: 437.2 $(M-H)^-$.

Example 8 rac-2-Ethoxy-3-[1-(5-methyl-2-o-tolyl-oxazol-4-ylmethyl)-1H-indol-4-yl]-propionic acid In analogy to the procedures described in examples 1 a] and 1 b], rac-2-ethoxy-3-(1H-indol-4-yl)-propionic acid ethyl ester was reacted with 4-chloromethyl-5-methyl-2-o-tolyl-oxazole in N,N-dimethylformamide in the presence of sodium hydride to yield rac-2-ethoxy-3-[1-(5-methyl-2-o-tolyl-oxazol-4-ylmethyl)-1H-indol-4-yl]-propionic acid ethyl ester, which was subsequently saponified to yield rac-2-ethoxy-3-[1-(5-methyl-2-o-tolyl-oxazol-4-ylmethyl)-1H-indol-4-yl]-propionic acid as light brown oil.

MS: 417.3 $(M-H)^-$.

Example 9 rac-3-{1-[2-(3-Chloro-phenyl)-5-methyl-oxazol-4-ylmethyl]-1H-indol-4-yl}-2-ethoxy-propionic acid In analogy to the procedures described in examples 1 a] and 1 b], rac-2-ethoxy-3-(1H-indol-4-yl)-propionic acid ethyl ester was reacted with 4-chloromethyl-2-(3-chloro-phenyl)-5-methyl-oxazole in N,N-dimethylformamide in the presence of sodium hydride to yield rac-3-{1-[2-(3-chloro-phenyl)-5-methyl-oxazol-4-ylmethyl]-1H-indol-4-yl}-2-ethoxy-propionic acid ethyl ester, which was subsequently saponified to yield rac-3-{1-[2-(3-chloro-phenyl)-5-methyl-oxazol-4-ylmethyl]-1H-indol-4-yl}-2-ethoxy-propionic acid as brown solid.

MS: 437.2 $(M-H)^-$.

Example 10 rac-2-Ethoxy-3-{1-[5-methyl-2-(4-trifluoromethyl-phenyl)-oxazol-4-ylmethyl]-1H-indol-4-yl}-propionic acid In analogy to the procedures described in examples 1 a] and 1 b], rac-2-ethoxy-3-(1H-indol-4-yl)-propionic acid ethyl ester was reacted with 4-chloromethyl-5-methyl-2-(4-trifluoromethyl-phenyl)-oxazole in N,N-dimethylformamide in the presence of sodium hydride to yield rac-2-ethoxy-3-{1-[5-methyl-2-(4-trifluoromethyl-phenyl)-oxazol-4-ylmethyl]-1H-indol-4-yl}-propionic acid ethyl ester, which was subsequently saponified to yield rac-2-ethoxy-3-{1-[5-methyl-2-(4-trifluoromethyl-phenyl)-oxazol-4-ylmethyl]-1H-indol-4-yl}-propionic acid as white solid.

MS: 471.3 (M−H)$^-$.

Example 11 rac-2-Ethoxy-3-{1-[2-(4-fluoro-3-methyl-phenyl)-5-methyl-oxazol-4-ylmethyl]-1H-indol-4-yl}-propionic acid In analogy to the procedures described in examples 1 a] and 1 b], rac-2-ethoxy-3-(1H-indol-4-yl)-propionic acid ethyl ester was reacted with 4-chloromethyl-2-(4-fluoro-3-methyl-phenyl)-5-methyl-oxazole in N,N-dimethylformamide in the presence of sodium hydride to yield rac-2-ethoxy-3-{1-[2-(4-fluoro-3-methyl-phenyl)-5-methyl-oxazol-4-ylmethyl]-1H-indol-4-yl}-propionic acid ethyl ester, which was subsequently saponified to yield rac-2-ethoxy-3-{1-[2-(4-fluoro-3-methyl-phenyl)-5-methyl-oxazol-4-ylmethyl]-1H-indol-4-yl}-propionic acid as off-white solid.

MS: 437.3 (M+H)$^+$.

Example 12 rac-2-Ethoxy-3-{1-[2-(4-isopropoxy-phenyl)-5-methyl-oxazol-4-ylmethyl]-1H-indol-4-yl}-propionic acid In analogy to the procedures described in examples 1 a] and 1 b], rac-2-ethoxy-3-(1H-indol-4-yl)-propionic acid ethyl ester was reacted with 4-chloromethyl-2-(4-isopropoxy-phenyl)-5-methyl-oxazole in N,N-dimethylformamide in the presence of sodium hydride to yield rac-2-ethoxy-3-{1-[2-(4-isopropoxy-phenyl)-5-methyl-oxazol-4-ylmethyl]-1H-indol-4-yl}-propionic acid ethyl ester, which was subsequently saponified to yield rac-2-ethoxy-3-{1-[2-(4-isopropoxy-phenyl)-5-methyl-oxazol-4-ylmethyl]-1H-indol-4-yl}-propionic acid as light yellow solid.

MS: 463.3 (M+H)$^+$.

Example 13 rac-2-Ethoxy-3-{1-[2-(4-isopropyl-phenyl)-thiazol-4-ylmethyl]-1H-indol-4-yl}-propionic acid In analogy to the procedures described in examples 1 a] and 1 b], rac-2-ethoxy-3-(1H-indol-4-yl)-propionic acid ethyl ester was reacted with 4-chloromethyl-2-(4-isopropyl-phenyl)-thiazole in N,N-dimethylformamide in the presence of sodium hydride to yield rac-2-ethoxy-3-{1-[2-(4-isopropyl-phenyl)-thiazol-4-ylmethyl]-1H-indol-4-yl}-propionic acid ethyl ester, which was subsequently saponified to yield rac-2-ethoxy-3-{1-[2-(4-isopropyl-phenyl)-thiazol-4-ylmethyl]-1H-indol-4-yl}-propionic acid as light brown solid.

MS: 449.3 (M+H)$^+$.

Example A

Tablets comprising the following ingredients can be manufactured in a conventional manner:

| Ingredients | Per tablet |
| --- | --- |
| Compound of formula I | 10.0–100.0 mg |
| Lactose | 125.0 mg |
| Maize starch | 75.0 mg |
| Talc | 4.0 mg |
| Magnesium stearate | 1.0 mg |

Example B

Capsules comprising the following ingredients can be manufactured in a conventional manner:

| Ingredients | Per capsule |
| --- | --- |
| Compound of formula I | 25.0 mg |
| Lactose | 150.0 mg |
| Maize starch | 20.0 mg |
| Talc | 5.0 mg |

Example C

Injection solutions comprising the following ingredients can be manufactured in a conventional manner:

| | |
| --- | --- |
| Compound of formula I | 3.0 mg |
| Gelatine | 150.0 mg |
| Sodium carbonate | to obtain a final pH of 7 |
| Phenol | 4.7 mg |
| Water for injection solutions | ad 1.0 ml |

What is claimed is:

1. A compound of formula (I)

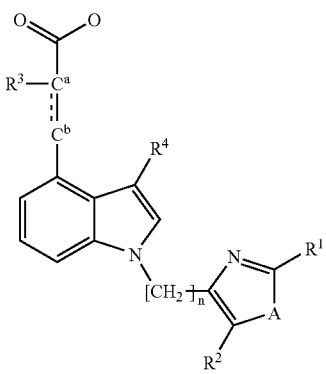

wherein

R$^1$ is unsubstituted naphthyl, unsubstituted phenyl, phenyl substituted with one or more substituents each independently selected from halogen, trifluoromethyl, amino, alkyl, alkoxy, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, hydroxy, alkyl substituted with one to three halogen atoms, and nitro,
unsubstituted heteroaryl which contains one or two hetero atoms selected from nitrogen, oxygen and sulfur,
or substituted heteroaryl which is heteroaryl which contains one or two hetero atoms selected from nitrogen, oxygen and sulfur and which is substituted on at least one carbon atom with a group independently selected from halogen, alkyl, alkoxy, cyano, haloalkyl and trifluoromethyl;

$R^2$ is hydrogen, alkyl or cycloalkyl;

$R^3$ is alkoxy or alkoxy substituted with one to three halogen atoms;

$R^4$ is hydrogen, alkyl or cycloalkyl;

A is oxygen or sulfur;

n is 1, 2 or 3;

wherein the bond between the carbon atoms $C^a$ and $C^b$ is a carbon carbon single or double bond;

and pharmaceutically acceptable salts and esters thereof.

2. The compound according to claim 1, wherein $R^1$ is unsubstituted phenyl or phenyl substituted with one or more substituents each independently selected from halogen, trifluoromethyl, amino, alkyl, alkoxy, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, hydroxy, alkyl substituted with one to three halogen atoms, and nitro.

3. The compound according to claim 2, wherein $R^1$ is unsubstituted phenyl or phenyl substituted with one to three substituents independently selected from the group consisting of alkoxy, alkyl, halogen and alkyl substituted with one to three halogen atoms.

4. The compound according to claim 3, wherein $R^1$ is selected from the group consisting of unsubstituted phenyl, dimethoxyphenyl, isopropyl-phenyl, fluoro-phenyl, chloro-phenyl, methyl-phenyl, trifluoromethyl-phenyl, methyl-fluoro-phenyl and isopropoxy-phenyl.

5. The compound according to claim 1, wherein $R^2$ is hydrogen or alkyl which is methyl or ethyl.

6. The compound according to claim 5, wherein $R^2$ is methyl.

7. The compound according to of claim 1, wherein $R^3$ is alkoxy which is methoxy or ethoxy.

8. The compound according to claim 1, wherein $R^4$ is hydrogen.

9. The compound according to claim 1, wherein the bond between the carbon atoms $C^a$ and $C^b$ is a carbon carbon single bond.

10. The compound according to claim 1, wherein n is 1 or 3.

11. The compound according to claim 1, wherein A is oxygen.

12. The compound according to claim 1 selected from the group consisting of:
rac-2-ethoxy-3-{1-[2-(4-isopropyl-phenyl)-5-methyl-oxazol-4-ylmethyl]-1H-indol-4-yl}-propionic acid;
rac-2-ethoxy-3-{1-[2-(5-methyl-2-phenyl-oxazol-4-yl)-ethyl]-1H-indol-4-yl}-propionic acid;
rac-2-ethoxy-3-[1-(5-methyl-2-phenyl-oxazol-4-ylmethyl)-1H-indol-4-yl]-propionic acid;
rac-2-ethoxy-3-{1-[2-(2-fluoro-phenyl)-5-methyl-oxazol-4-ylmethyl]-1H-indol-4-yl}-propionic acid; and
rac-3-{1-[2-(2-chloro-phenyl)-5-methyl-oxazol-4-ylmethyl]-1H-indol-4-yl}-2-ethoxy-propionic acid.

13. The compound according to claim 1 selected from the group consisting of:
rac-2-ethoxy-3-[1-(5-methyl-2-o-tolyl-oxazol-4-ylmethyl)-1H-indol-4-yl]-propionic acid;
rac-3-{1-[2-(3-chloro-phenyl)-5-methyl-oxazol-4-ylmethyl]-1H-indol-4-yl}-2-ethoxy-propionic acid;
rac-2-ethoxy-3-{1-[5-methyl-2-(4-trifluoromethyl-phenyl)-oxazol-4-ylmethyl]-1H-indol-4-yl}-propionic acid;
rac-2-ethoxy-3-{1-[2-(4-isopropoxy-phenyl)-5-methyl-oxazol-4-ylmethyl]-1H-indol-4-yl}-propionic acid; and
rac-2-ethoxy-3-{1-[2-(4-isopropyl-phenyl)-thiazol-4-ylmethyl]-1H-indol-4-yl}-propionic acid.

14. The compound according to claim 1, rac-3-{1-[2-(3,5-dimethoxy-phenyl)-5-methyl-oxazol-4-ylmethyl]-1H-indol-4-yl}-2-ethoxy-propionic acid.

15. The compound according to claim 1, rac-2-ethoxy-3-{1-[3-(5-methyl-2-phenyl-oxazol-4-yl)-propyl]-1H-indol-4-yl}-propionic acid.

16. The compound according to claim 1,
rac-2-ethoxy-3-{1-[2-(4-fluoro-3-methyl-phenyl)-5-methyl-oxazol-4-ylmethyl]-1H-indol-4-yl}-propionic acid.

17. A pharmaceutical composition comprising a compound or a pharmaceutically acceptable salt thereof in accordance with claim 1 and a therapeutically inert carrier.

18. The pharmaceutical composition of claim 16 further comprising a therapeutically effective amount of orlistat.

19. A method for treatment of non-insulin dependent diabetes mellitus in a patient in need of treatment, comprising administering to said patient an effective amount of from about 0.1 mg to about 1000 mg per day of a compound or a pharmaceutically acceptable salt thereof according to claim 1.

20. The method according to claim 19, which further comprises administering to said patient an effective amount of from 60 mg to 720 mg per day of orlistat.

* * * * *